United States Patent
Ginzburg et al.

(10) Patent No.: US 7,412,283 B2
(45) Date of Patent: Aug. 12, 2008

(54) METHOD AND SYSTEM FOR PROCESSING ELECTROCARDIAL SIGNALS

(76) Inventors: Aaron Ginzburg, 5/74 Hawthorn Road, Caulfield North, Vic 3161 (AU); Andrew Maxwell Tonkin, 45 Hawke Street, West Melbourne, Vic 3003 (AU); John David Horowitz, 50 Park Road, Kensington Park S.A. 5068 (AU); Alexander Tsintsiper, 34 Cluden Street, East Brighton, Vic. 3187 (AU)

( * ) Notice: Subject to any disclaimer, the term of this patent is extended or adjusted under 35 U.S.C. 154(b) by 332 days.

(21) Appl. No.: 10/865,985

(22) Filed: Jun. 11, 2004

(65) Prior Publication Data

US 2005/0027202 A1      Feb. 3, 2005

(30) Foreign Application Priority Data

Nov. 28, 2001  (AU) .................................. PR9165/0
Nov. 13, 2002  (AU) .............................. 2002302003

(51) Int. Cl.
*A61B 5/04*        (2006.01)
(52) U.S. Cl. ..................................................... 600/517
(58) Field of Classification Search ......... 600/508–528; 128/923

See application file for complete search history.

(56) References Cited

U.S. PATENT DOCUMENTS

| | | | | |
|---|---|---|---|---|
| 3,616,791 A | * | 11/1971 | Harris ......................... 600/515 |
| 4,041,468 A | * | 8/1977 | Perry et al. ................. 600/523 |
| 4,457,315 A | * | 7/1984 | Bennish ....................... 600/517 |
| 4,492,235 A | | 1/1985 | Sitrick |
| 4,680,708 A | | 7/1987 | Ambos et al. |
| 4,802,491 A | | 2/1989 | Cohen et al. |
| 4,958,641 A | * | 9/1990 | Digby et al. ................. 600/515 |
| 5,020,540 A | | 6/1991 | Chamoun |
| 5,029,082 A | | 7/1991 | Shen et al. |
| 5,092,341 A | * | 3/1992 | Kelen ........................... 600/515 |
| 5,109,862 A | * | 5/1992 | Kelen et al. ................. 600/515 |
| 5,215,099 A | | 6/1993 | Haberl et al. |
| 5,348,020 A | | 9/1994 | Hutson |

(Continued)

FOREIGN PATENT DOCUMENTS

JP       63-270026       11/1988

(Continued)

*Primary Examiner*—Carl H. Layno
*Assistant Examiner*—Jessica Reidel
(74) *Attorney, Agent, or Firm*—Sheridan Ross P.C.

(57) ABSTRACT

Known methods of heart function analysis, while useful, suffer from a number of limitations. These include the fact that these methods are inherently static, in that they consider an individual electrocardiogram (ECG) that can only provide a picture of heart function at a particular moment in time. Furthermore, the assessment depends upon the expertise of specialists performing a visual analysis of ECG traces, which may be subjective, and of limited sensitivity. Accordingly, a method of processing ECG signals comprises the steps of extracting data from at least one ECG signal, determining a time derivative of the data and generating a normalised index value representative of the energy in the time derivative. The index value is compared with corresponding historical data of the patient. The index may be used as an objective indication of heart function, and recorded for an individual patient over a period of time as a dynamic record of any change in heart function of the patient that may be indicative of abnormal function or heart disease.

41 Claims, 7 Drawing Sheets

U.S. PATENT DOCUMENTS

| | | | |
|---|---|---|---|
| 5,423,326 A * | 6/1995 | Wang et al. | 600/526 |
| 5,474,078 A | 12/1995 | Hutson | |
| 5,609,158 A | 3/1997 | Chan | |
| 5,655,540 A * | 8/1997 | Seegobin | 600/515 |
| 5,769,793 A | 6/1998 | Pincus et al. | |
| 5,782,876 A | 7/1998 | Flammang | |
| 6,029,087 A | 2/2000 | Wohlgemuth | |
| 6,047,206 A | 4/2000 | Albrecht et al. | |
| 6,169,919 B1 | 1/2001 | Nearing et al. | |
| 7,218,960 B1 * | 5/2007 | Min et al. | 600/509 |
| 2001/0020136 A1 * | 9/2001 | Sweeney et al. | 600/515 |
| 2003/0013978 A1 | 1/2003 | Schlegel et al. | |
| 2003/0060724 A1 | 3/2003 | Thiagarajan et al. | |
| 2003/0097075 A1 * | 5/2003 | Kuo | 600/500 |
| 2003/0208129 A1 | 11/2003 | Beker et al. | |
| 2004/0044292 A1 | 3/2004 | Yasushi et al. | |
| 2004/0215090 A1 * | 10/2004 | Erkkila et al. | 600/515 |

FOREIGN PATENT DOCUMENTS

| | | |
|---|---|---|
| TW | 555545 | 10/2003 |
| WO | WO 93/04627 | 3/1993 |
| WO | WO 94/10905 | 5/1994 |
| WO | WO 97/24062 | 7/1997 |
| WO | WO 01/34023 A1 | 5/2001 |
| WO | WO 03/024323 A1 | 3/2003 |

* cited by examiner

METHOD AND SYSTEM FOR PROCESSING ELECTROCARDIAL SIGNALS

FIELD OF THE INVENTION

The present invention relates to a method and system for processing electrocardial signals. In particular, the method and system is well suited to processing complexes and/or segments of a standard 12-lead ECG.

BACKGROUND OF THE INVENTION

Heart disease is one of the major causes of death in the world today. Health care costs associated with cardiovascular disease exceed those of any other disease. Sudden cardiac death (unexpected death due to a cardiac malfunction within a short time period from the onset of symptoms in an individual who would otherwise be considered to be a normal, healthy adult) is often the first manifestation of heart disease.

More than one in five heart attacks in people over the age of 65 are unrecognised, according to a study published in the January 2000 issue of the Journal of the American College of Cardiology. Of the 901 subjects in whom an electrocardiogram indicated a prior heart attack, more than one fifth had had heart attacks that had gone undetected until the test was conducted. Most patients had no clear indication of cardiovascular disease when they commenced the study. Lack of recognition may be based upon the true absence of symptoms (probably rare), unusual symptoms (for example, shortness of breath without chest pain) or misinterpretation of symptoms (for example, attribution of chest pain to "indigestion").

Silent heart attacks are an extreme case of a condition called "silent ischemia", which is a chronic shortage of oxygen and nutrients to a portion of the heart. Occurrences of silent ischemia increase the risk of sudden cardiac death.

The cause of ischemia, silent or otherwise, is almost always atherosclerosis—the progressive narrowing of the arteries to the heart from accumulations of cholesterol plaque. In most instances, this reduction in blood supply generates a "protest" from the heart—typically a crushing sensation called angina. However, in up to 30 percent of heart attack victims there are no previous symptoms associated with such blockages. This underscores the importance of early detection of coronary artery disease. Indeed, the Framingham heart study, which has followed 4,000 Massachusetts men for more than 40 years, has found that 25 percent of their subjects' heart attacks go unnoticed until their annual electrocardiograms detected the after-effects of those attacks.

Because these silent heart attacks go undetected, they cannot be treated early. This increases the chance of further—sometimes fatal—complications. According to the National Heart Foundation report (1999), 40% of sudden cardiac deaths are unpredictable, suggesting that many people are effectively carrying a time bomb. Almost 50% of heart attacks occur among people who have normal cholesterol, low blood pressure and are in good physical shape. For many people sudden death is the first manifestation of heart disease. Therefore early awareness and recognition are important to prevent sudden cardiac death.

There is no way of predicting with certainty who is a candidate for silent ischemia, but statistically, the greater the number of risk factors a patient possesses the more likely that he or she is a candidate. Not all cases of sudden cardiac death result from "heart attacks". For example, patients with poorly functioning hearts are at risk of dangerous rhythm abnormalities. These life-threatening events may occur with few preceding symptoms. To be able to detect heart disease at an early stage is of great importance.

The basic tool for evaluation of the health of the human heart is the standard 12-lead electrocardiogram (ECG), which records the electrical activity of the heart, as detected by electrodes, located at established locations on the body surface, to which the leads are attached. The ECG is a commonly used cardiac diagnostic tool. Medical practitioners and cardiologists alike use the ECG to observe the electrical activity of the heart for determining whether any indications as to heart disease exist. It is thus widely accepted that the ECG is an extremely useful and, importantly, non-invasive diagnostic tool. Indeed, it is the only practical non-invasive method of recording the electrical activity of the heart, and importantly, it is the first laboratory test performed in a patient with chest pain, syncope or presyncope, the two major markers of potential cardiovascular catastrophe.

The ECG reflects an electrical phenomenon that can be altered identically by a variety of functional and anatomic disorders. It is recognised, however, that the resting ECG is not a very sensitive or specific marker for occult heart disease, and accordingly the prognostic value of many ECG abnormalities is unclear. Limitations of the use of the ECG for diagnosis include the difficulty of recognising small changes in voltage and time intervals, and the dependence upon deductive analysis by a specialist. Furthermore, intracardiac studies demonstrate that changes of conduction or cycle length in the order of few milliseconds may result in delay or blockage of an impulse, and such changes may not be evident from a surface ECG.

The available methods of ECG analysis are presently limited, and current diagnostic procedures are largely based on visual interpretation of the ECG signal by a skilled medical practitioner. Such interpretation of the ECG is a process requiring detailed visual analysis of the frequency and amplitude of signal elements and signal patterns representing the heart muscle function in operation. Furthermore, reading an individual ECG only provides an indication of heart function at a particular moment in time, and is highly dependent upon the expertise and experience of the medical practitioner viewing a print of the patient's ECG signal. The process of manually analysing an ECG signal may be time consuming, and is to a large extent subjective.

Presently, the most common form of assessment is based on an analysis of the resting ECG. However, it is known that patients with clinically significant coronary artery disease often have a normal resting ECG. Further, clinical studies have shown that 25% to 50% of patients with a history of chest pain due to documented coronary artery disease have normal resting ECG when they are pain free.

Known methods of heart assessment are generally based on the visual analysis of the resting ECG in the time domain. The technique involves consideration of the shape of the various complexes and segments making up the ECG waveform, and the counting of features such as notches and/or slurs in an ECG trace. The technique may also include investigation of such parameters as conduction intervals of electrocardial signals through the tissue. Such features and parameters may only become visible to the experienced medical practitioner or cardiologist once a problem is already present that signifies irreversible pathology.

Figure 1:
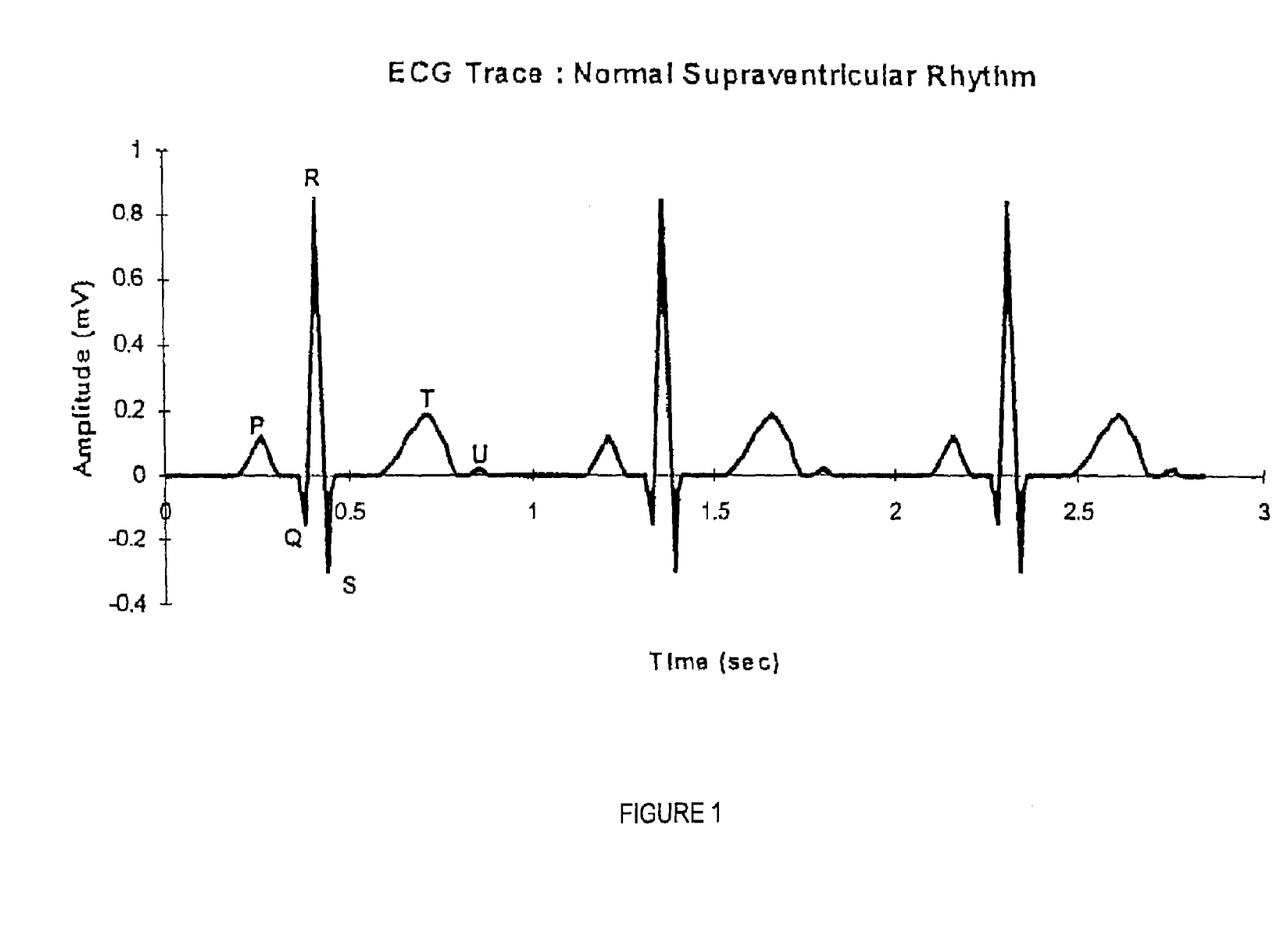
FIG. 1 is an example ECG trace of a normal supraventricular rhythm of a human heart.

An example human ECG is shown in FIG. 1. As can be seen, the heart rhythms traced by the ECG are rhythmic and repeating. The variation in amplitude of the electrical signal is due to the polarisation and depolarisation of different areas of the heart as part of each rhythmic pumping cycle. While the ECG generated depends on numerous factors, a skilled cardiologist will nonetheless often be able to notice anomalies in an otherwise normal looking ECG. However, reading an individual ECG effectively provides only a "static" picture of the heart function over a particular short time period, such as a few minutes, and does not allow for analysis of historical trends in a patient's heart function.

The ECG trace shown in FIG. 1 details several peaks and troughs in the amplitude of the electrical signals associated with the normal supraventricular rhythm and these are labelled sequentially with the letters P, Q, R, S, T and U within each rhythmic period. Analysis of the amplitude characteristics of particular parts of the rhythm can provide information concerning heart function for particular parts of the heart pumping cycle. The portion of the cycle which starts at the beginning of the trough marked Q and ends after the trough marked S is termed the "QRS complex" or "QRS interval". It is known that the prolongation or shortening of the QRS complex relates to changes in the ventricular conduction velocity within the His-Purkinje system and indicates pathological processes associated with ischemia or infarction. The accuracy of QRS interval determination presents a problem concerning time domain analysis of ventricular rhythms. Visual estimation of the duration of the QRS complex can be relatively accurate for approximation purposes, but precise localisation of onset and offset of the QRS complex to within a few milliseconds can be difficult, particularly at more rapid heart rates and where signal noise is present. QRS interval measurements derived from visual estimation may also be affected by different abilities among medical practitioners and consequent limitations in subjective accuracy.

The portion of the cycle which starts at the beginning of the trough marked S and ends at the peak marked T is termed the "ST segment". Traditionally, changes to the ST segment and the T wave have been utilized for detection of myocardial ischemia or infarction. In considering the ST segment, most practitioners employ one of two standards for determining the portion of the ECG waveform for closest analysis. The first of these standards involves consideration of the period of 60 milliseconds following the point S of the ECG waveform, whereas the alternative standard involves consideration of the period of 80 milliseconds following this point.

Of course, other complexes and/or segments of the ECG waveform also include information relevant to the analysis of heart function.

In view of the aforementioned limitations of conventional time domain analysis, spectral evaluation of the ECG signal in the frequency domain has been proposed. However, no method of spectral evaluation as yet been widely accepted as an alternative to the conventional analysis.

Further methods of ECG analysis that have been studied include those directed to variability in heart rate, detection of late potentials, changes in R wave amplitudes, and various spectral mapping techniques. As yet, none of these have been found to be as useful or effective for assessment of heart function as current methods, and their clinical use is as yet unproven.

Accordingly, known methods of heart function analysis while useful, suffer from a number of limitations. These include the fact that these methods are inherently static, in that they consider an individual ECG that can only provide a picture of heart function at a particular moment in time. Furthermore, the assessment depends upon the expertise of specialists performing a visual analysis of ECG traces, which may be subjective, and of limited sensitivity. Furthermore, in order to facilitate such visual assessment, standard equipment incorporates filters and/or amplifiers, which may exclude potentially significant information and/or obscure signals of interest. It may be difficult to discriminate between noise and signs of possible disfunction such as late potentials. Additionally, inconsistent definitions of abnormal findings may be applied by different medical practitioners.

However, despite these limitations, improved methods of non-invasive heart monitoring have yet to be widely introduced.

In light of the above, it is desired to provide a method and system which enables objective analysis of ECG data relating to complexes and/or segments of the ECG signal by providing a numerical indication concerning heart function. Such an indication would assist medical practitioners to determine whether a patient may be at risk of being affected by heart disease.

Any discussion of documents, devices, acts or knowledge in this specification is included to explain the context of the invention. It should not be taken as an admission that any of the material formed part of the prior art base or the common general knowledge in the relevant art on or before the priority date of the claims herein.

SUMMARY OF THE INVENTION

In one aspect, the present invention provides a method of processing ECG signals comprising the steps of:

extracting data from at least one ECG signal;

determining a time derivative of said data; and generating a normalised index value representative of the energy in said time derivative.

Accordingly, the invention provides for the generation of a single index value from an ECG signal, that is characteristic of the signal and therefore of the current heart function of the patient. A particular benefit of the invention is that this index may be monitored dynamically over a period of time in order to observe historical trends in the index. Any substantial changes in the magnitude of the index for a particular patient may be indicative of changes in heart function of the patient, and may therefore be used to alert a medical practitioner to the possibility of abnormal heart function requiring further investigation and diagnosis. Changes in the ECG signal that result in substantial changes in the index value may not be readily observable by visual inspection of the ECG trace, and the index may therefore be used as an early indicator of possible heart dysfunction.

The step of generating a normalised index value preferably comprises:

determining frequency components of said time derivative; and calculating a normalised index value representative of the energy in said frequency components.

It is particularly preferred that the step of determining frequency components includes computing a Fourier transform of said time derivatives. Preferably, said Fourier transform is a discrete Fourier transform, and in a particularly preferred embodiment is a 512 point discrete Fourier transform. Improved efficiency of an implementation of the method may be realised when the discrete Fourier transform is computed using a Fast Fourier Transform (FFT) algorithm.

In preferred embodiments, the step of calculating a normalised index value comprises calculating a normalised sum of the squares of the magnitudes of said frequency components.

The ECG signals may comprise signals from any one or more of up to 12 leads of a standard 12-lead ECG recorder.

It is preferred that said normalised index value is computed according to:

$$\text{normalised index value} = \sum_R \left\{ \frac{1}{n} \sum_{i=1}^{n} F_i^2 \right\}$$

wherein:

R represents one or more of up to 12 leads of a standard 12-lead ECG;

$F_i$ represents the magnitude of frequency components of said time derivative; and n is the total number of said frequency components.

The step of extracting preferably comprises the steps of:

determining the times of onset and termination of selected complexes and/or segments of said ECG signals; and copying each of said selected complexes and/or segments into a data record to create said extracted data.

The selected complexes and/or segments may comprise QRS complexes of said ECG signals.

In some embodiments of the method, the step of determining the times of onset and termination of a selected QRS complex comprises identifying local minima in the ECG signal corresponding to the points Q and S according to the equations:

$$A(t_{q-3}), A(t_{q-2}), A(t_{q-1}) > A(t_q) < A(t_{q+1}), A(t_{q+2}), A(t_{q+3})$$

$$A(t_{s-3}), A(t_{s-2}), A(t_{s-1}) > A(t_s) < A(t_{s+1}), A(t_{s+2}), A(t_{s+3})$$

wherein $A(t_i)$ is an amplitude of the ECG signal at the time corresponding to the $i^{th}$ sample point, $t_q$ is the time of onset of the QRS complex corresponding to the point Q, and $t_s$ is the time of termination of the QRS complex corresponding to the point S.

The ECG signals preferably comprise signals from any one or more of up to 12 leads of a standard 12-lead ECG. In preferred embodiments, the invention thus provides the advantage of being compatible with existing standard ECG recording equipment.

A standard duration of a selected QRS complex may be determined for each of said leads as the average of the time intervals between the time of onset and the time of termination of a plurality of ECG signals received from each of said leads.

Alternatively, a standard duration of a selected QRS complex may be one of 60 milliseconds, 80 milliseconds, 100 milliseconds or 120 milliseconds, and the times of onset and termination of said selected QRS complex may be determined such that the selected complex is centred on an R peak of the ECG signal.

The selected complexes and/or segments may alternatively comprise ST segments of ECG signals.

The onset of said ST segments may be determined as the time $t_s$ of a local minimum in the ECG signal corresponding to point S according to the equation:

$$A(t_{s-3}), A(t_{s-2}), A(t_{s-1}) > A(t_s) < A(t_{s+1}), A(t_{s+2}), A(t_{s+3})$$

wherein $A(t_i)$ is an amplitude of the ECG signal at the time corresponding to the $i^{th}$ sample point.

In preferred embodiments, the duration of each of said ST segments is either 60 milliseconds or 80 milliseconds.

If will therefore be appreciated that, in at least preferred embodiments, the invention enables a complex and/or segment of the ECG signal to be identified and selected in a fully automated manner, and that accordingly no specialised expertise is required to inspect and interpret the ECG trace in order to compute the normalised index.

In particularly preferred embodiments, said step of extracting includes sampling said ECG signaling data to provide digitized ECG signals. Said sampling is preferably carried out at a sample rate of approximately 1000 Hz.

In another aspect, the present invention provides an apparatus for processing ECG signals comprising:

an extractor for extracting data from at least one ECG signal;

a differentiator for determining a time derivative of said data; and an index value generator for generating a normalised index value representative of the energy in said time derivative.

The generator preferably comprises:

a spectrum calculator for determining frequency components of said time derivative; and an index value calculator for calculating a normalised index value representative of the energy in said frequency components.

In a preferred embodiment, the spectrum calculator determines frequency components of said time derivative by computing a Fourier transform of said time derivative using a Fast Fourier Transform (FFT) algorithm, and the index value calculator calculates a normalised sum of the squares of the magnitudes of the frequency components determined by the spectrum calculator.

The ECG signals may comprise signals from any one or more of up to 12 leads of a standard 12-lead ECG, and the index value generator preferably computes a normalised index value according to the equation:

$$\text{normalised index value} = \sum_R \left\{ \frac{1}{n} \sum_{i=1}^{n} F_i^2 \right\}$$

wherein:

R represents one or more of up to 12 leads of a standard 12-lead ECG;

$F_i$ represents the magnitude of frequency components of said time derivative; and n is the total number of said frequency components.

The extractor preferably determines the times of onset and termination of selected complexes and/or segments in said ECG signals, and copies each of said selected complexes and/or segments sequentially into a data record to create said extracted data.

The selected complexes and/or segments may comprise QRS complexes or ST segments of said ECG signals.

In yet another aspect, the present invention provides a method of identifying possible abnormalities of heart function of a patient comprising:

extracting data from each of a plurality of ECG signals of said patient gathered over a plurality of respective time periods;

determining a plurality of respective time derivatives of said extracted data;

generating a plurality of respective normalised index values representative of the energy in said time derivatives; and comparing said normalised index values over said plurality of time periods to identify possible abnormalities of heart function of said patient.

In preferred embodiments, the step of comparing includes calculating a mean value of said normalised index values, an upper bound value above said mean value, and a lower bound value below said mean value, and comparing each of said normalised index values with said upper and lower bound values to identify possible abnormalities of heart function of said patient. It is preferred that the upper and lower bound values are calculated as values representing a specified fractional deviation from said mean value. The fractional deviation may be, for example, a 10% deviation.

The step of comparing preferably includes generating a graph of said normalised index values as a function of time. Also preferably, the graph includes indications of said mean value, said upper bound value and said lower bound value.

The step of comparing preferably includes identifying possible abnormalities of heart function of said patient if one or more said normalised index values falls outside the range bounded by said upper and lower bound values.

In still another aspect, the present invention provides a system for identifying possible abnormalities of heart function of a patient comprising:

an extractor for extracting data from each of a plurality of ECG signals of said patient gathered over a plurality of respective time periods;

a differentiator for determining a plurality of respective time derivatives of said extracted data;

an index value generator for generating a plurality of respective normalised index values representative of the energy in said time derivatives; and an index value comparator for comparing said normalised index values over said plurality of time periods to identify possible abnormalities of heart function of said patient.

The system preferably comprises a computer having a display, and said index value comparator is preferably configured to generate a graph of said normalised index values as a function of time on said display.

The index value comparator may further be configured to calculate a mean value of said normalised index values, an upper bound value above said mean value, and a lower bound value below said mean value, and to include indications of said mean value, said upper bound value, and said lower bound value in the graph displayed on said display.

In a further aspect, the present invention provides a system for processing ECG signals of a patient comprising:

a server computing system configured to receive digitized ECG signals over a data network, and including a processor configured to form the steps of:

extracting data from at least one ECG signal;

determining a time derivative of said extracted data; and generating a normalised index value representative of the energy in said time derivative, and a database associated with said server for storing said normalised index value and/or digitized ECG signals in a data record of said patient.

In a still further aspect, the present invention provides a system for gathering ECG signals of a patient for processing, said system comprising:

ECG apparatus for monitoring and digitizing ECG signals of said patient; and a client computing system configured to receive digitized ECG signals from said ECG apparatus, and to transmit said digitized ECG signals over a data network to a server computing system, said server including a processor configured to perform the steps of:

extracting data from said digitized ECG signal;

determining a time derivative of said extracted data; and generating a normalised index value representative of the energy in said time derivative.

Preferably, the client is further configured to receive one or more generated normalised index values from said server, and to display a graph of said normalised index values to enable a user of said client to identify possible abnormalities of heart function of said patient.

BRIEF DESCRIPTION OF THE DRAWINGS

Preferred embodiments of the present invention will now be described, without limitation upon the overall scope of the invention, with reference to the accompanying drawings in which.

DETAILED DESCRIPTION OF EMBODIMENTS OF THE INVENTION

Figure 2:
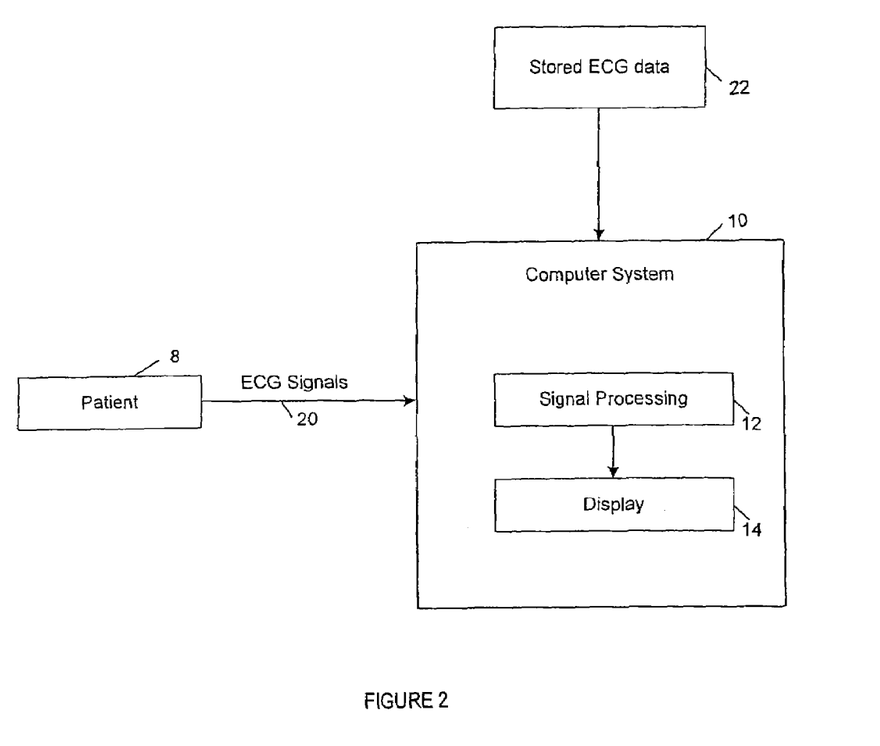
FIG. 2 is a block diagram of a system for processing electrocardial signals.

Referring to FIG. 2, a computer system 10 for executing information processing according to embodiments of the invention is provided with a signal processor 12 and display module 14. The computer system 10 is adapted to receive ECG signals 20 from a patient 8 as noisy analogue signals. These analogue signals may be conditioned according to normal ECG signal conditioning techniques to place the signals 20 in a form which is suitable for digital sampling and are stored in the computer system at least temporarily but preferably in non-volatile memory. The ECG signals 20 are derived from one or more of up to twelve leads of the standard 12-lead ECG, and preferably include ECG signals from all twelve leads.

The signal processor 12 is configured to sample the ECG signals 20 at a rate of about 1000 Hz for digitisation thereof. The signal processor 12 then extracts the digitised samples corresponding to a selected complex and/or segment within the ECG signals 20 such as the QRS complex or ST segment, either randomly selecting spaced complexes and/or segments within the time period over which the ECG signals 20 were read from the patient 8, or by extracting consecutive sequences of such complexes and/or segments. Further processing of the digitised ECG signals 20 is described below. The signal processor 12 outputs to the display module 14 a normalised index value calculated from the processed ECG signals 20 and this can be viewed through an interface 100 such as that exemplified in FIG. 4, where normalised index values from other samples of ECG signals 20 can be viewed for comparison. The normalised index value (the derivation method of which is described later) is hereinafter referred to as the HeartGuard Index (HGI) value.

Although the signal processor 12 is shown in FIG. 2 as a single element, it is made up of a collection of hardware and software modules, which are available commercially.

As an alternative to receiving as input the ECG signals 20, the computer system 10 may receive stored ECG data 22 as input. The stored ECG data 22 may be stored on a storage medium local to the computer system 10 or in a database (such as ECG database 60 shown in FIG. 3) in communication with the computer system 10. As a further alternative the stored ECG data 22 may be stored remotely and transmitted to the computer system 10 over a network such as the Internet.

Figure 5:
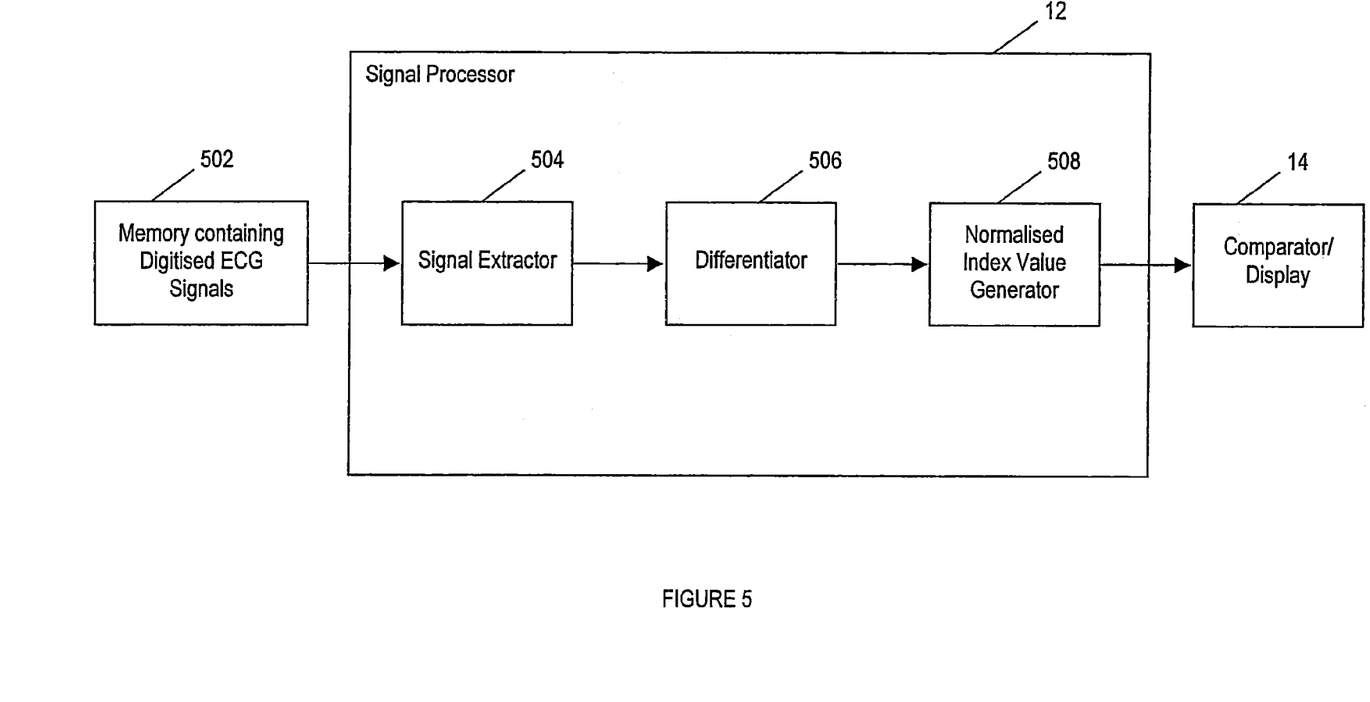
FIG. 5 is a block diagram of an apparatus for processing ECG signals according to a preferred embodiment of the invention.

The process of generating HGI values is now described with reference to FIG. 5. The figure shows a block diagram of the signal processor 12, in which the main signal processing elements are illustrated in greater detail. In a preferred embodiment, each signal processing element is implemented as a software module and may be implemented using available signal processing toolkits, applications and/or libraries.

A standard 12-lead electrocardiogram is recorded by a common ECG recorder and saved onto computer memory 502. Any selected complex and/or segment of the unfiltered ECG from one or more of up to twelve leads of the standard 12-lead ECG, may be the subject of the presently described numerical analysis. In the following description, analysis of the QRS complex and ST segment is described by way of example. The ECGs from each of these leads are recorded for approximately two minutes. The recorded signals may be digitised using any suitable commercially available analog/digital hardware, preferably with 16-bit accuracy at a sampling rate of 1000 Hz, and saved on the computer system 10 for later analysis. It will be appreciated by those skilled in the art that ECG recorders are available commercially that include the necessary and log/digital conversion hardware, and that accordingly are able to provide the signals to computer system 10 in a suitable digital form.

A single QRS complex of the digitised ECG waveform may be identified by determination of the onset and termination by comparison of the respective amplitude values which are smaller than those of at least three preceding and three following neighbouring points, respectively. This effectively means that the minimum of the Q and S troughs are selected as the onset and termination points. The times $t_q$ and $t_s$ of onset and termination respectively of the QRS complex are determined as follows:

$$A(t_{q-3}), A(t_{q-2}), A(t_{q-1}) > A(t_q) < A(t_{q+1}), A(t_{q+2}), A(t_{q+3})$$

$$A(t_{s-3}), A(t_{s-2}), A(t_{s-1}) > A(t_s) < A(t_{s+1}), A(t_{s+2}), A(t_{s+3})$$

wherein $A(t_i)$ is an amplitude of the ECG signal at the time corresponding to the $i^{th}$ sample point, $t_q$ is the time of onset of the QRS complex corresponding to the point Q, and $t_s$ is the time of termination of the QRS complex corresponding to the point S.

The individual QRS complexes thus identified are then extracted by signal extractor 508, which copies them into a new data record containing only the selected QRS complexes. The identified QRS complexes may be extracted in sequence or instead a random selection of identified QRS complexes may be extracted.

The first derivatives of the multiple QRS complexes of the unfiltered signal-averaged ECG are then calculated by differentiator 506. The normalised index value generator 508 computes a normalised index value that is representative of the energy in the time derivative. In a particularly preferred embodiment of the invention, the normalised index value generator 508 first determines frequency components of the time derivative, and then calculates a normalised index value representative of the energy in the frequency components. Specifically, the normalised index value is preferable a normalised sum of the squares of the magnitudes of the frequency components.

Figure 6:
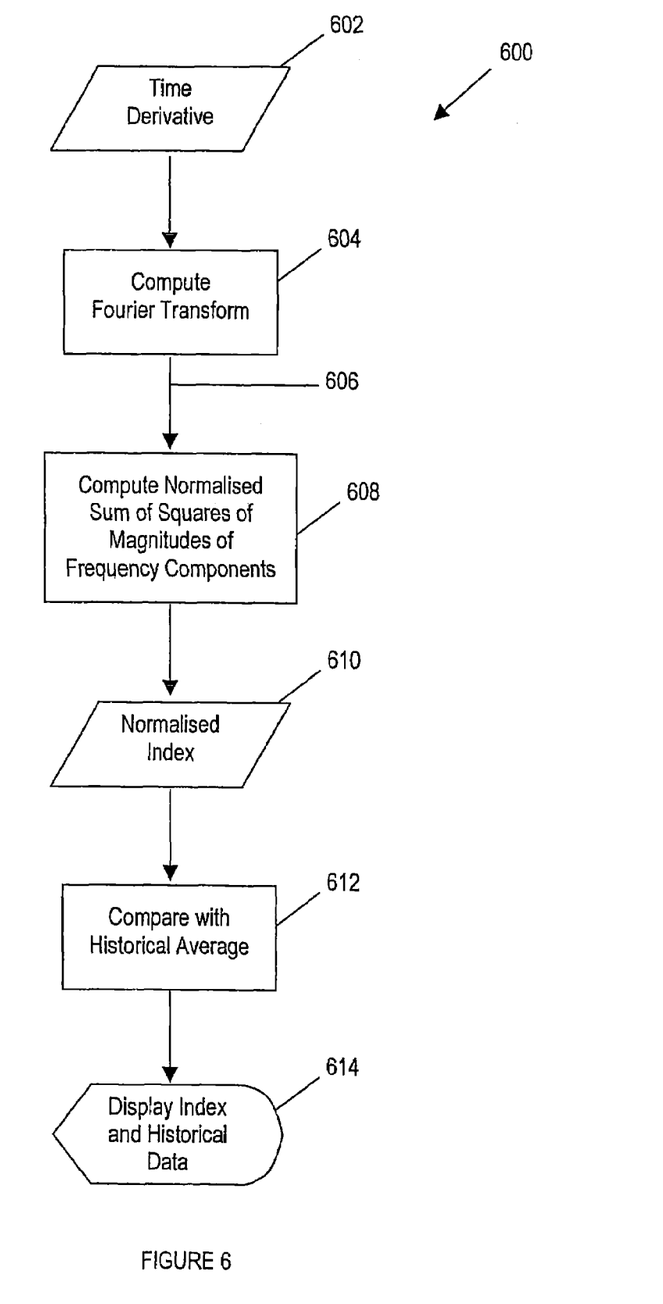
FIG. 6 is a flow chart illustrating a preferred method of computing a normalised index value in accordance with the invention.

The preferred method of computing the normalised index value is illustrated in the flow chart of FIG. 6. The input to the process is the calculated time derivative 602, which in a preferred embodiment consists of 512 samples of the extracted signal constructed by the signal extractor 504. A 512-point Fast Fourier Transform (FFT) is then performed 604 on the entire set of QRS extracted complexes of the surface ECG. The FFT is performed on the QRS complexes of each of the chosen leads. The magnitudes $F_i$ of the FFT-transform data 606 are then squared, summed and normalised 608 to obtain the normalised energy 610 EQRS value of the computed high-frequency signal from each of the leads, as follows:

$$E_{QRS} = (1/N) \sum_{i=1}^{n} F_i^2 \quad (n = 512).$$

Figure 7A:
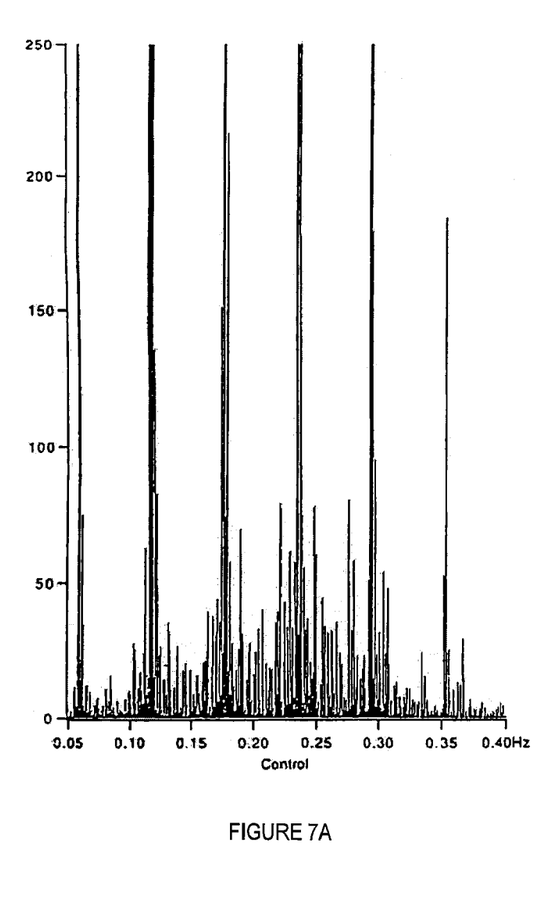
FIGS. 7A and 7B are charts illustrating the differences in the spectral patterns for normal (control) and abnormal (induced ischemia) heart function during two stages of animal study, the spectra being computed in accordance with a preferred embodiment of the invention.
Figure 7B:
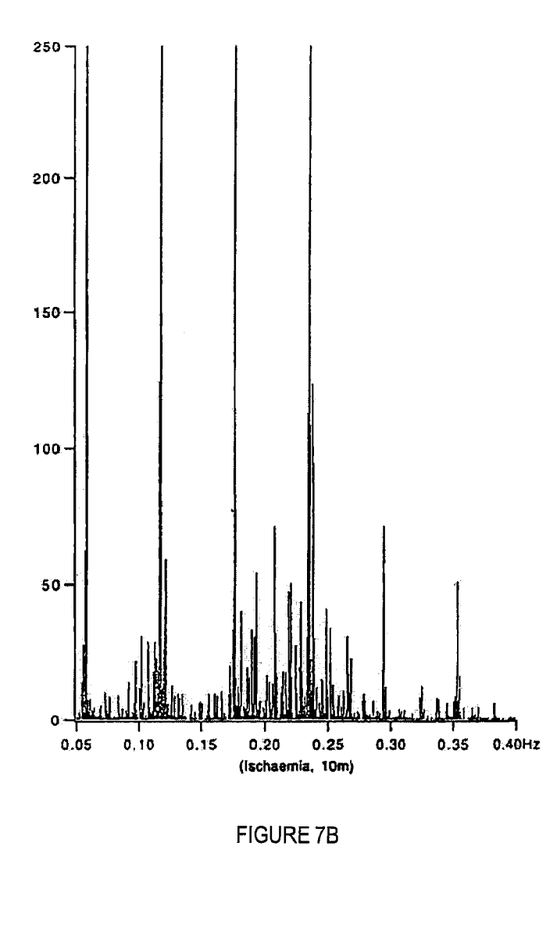

The significance of considering the time derivative data in the frequency domain may be appreciated from the corresponding frequency spectra shown in FIGS. 7A and 7B. FIG. 7A shows the calculated frequency spectrum of the time derivative of the extracted QRS complexes of a particular subject with normal heart function. The subject in this case is a greyhound as studied in the preclinical animal studies. FIG. 7B shows the calculated spectrum for the same subject with an induced ischemia. Comparison of the spectra of FIG. 7A and 7B clearly reveals the reduction in energy in the spectrum, and in particular in the magnitude of the higher frequency peaks of the spectrum. Accordingly, the energy in the time derivative, as preferably observed by way of the calculated frequency spectrum, could be a good indicator of abnormal heart function.

The HGI is determined as a mathematical summation of normalised energy values over the elected leads and expressed as follows:

$$HGI = \sum_{R} \left\{ (1/n) \sum_{i=1}^{n} F_i^2 \right\}, \quad (n = 512).$$

where R represents one or more of up to 12 leads of a standard 12-lead ECG, conventionally labelled I, II, III, avR, avL, avF, $V_1$, $V_2$, $V_3$, $V_4$, $V_5$ and $V_6$. A global HGI value, $HGI_G$, is defined to be the HGI value computed over all 12 leads. It will be understood that individual HGI values, referred to as regional HGI values ($HGI_R$), may be computed for each individual lead, and that corresponding HGI values may be computed for any chosen combination of leads.

Alternative values of n can be used for the FFT and subsequent calculations, such as 256, 1024 or other powers of 2.

As previously described, the signal extractor 504 is required to extract a random selection, or more preferably a sequence, of identified QRS complexes. It will be appreciated that since the ECG signal is derived in real time from a patient, the relative times of onset and termination, and hence the length, of each sequential QRS complex may not be identical. However, it may be inconvenient for the signal extractor 504 to construct a data record consisting of selected complexes of varying length, and it is not anticipated that the method of the present invention is particularly sensitive to the precise determined times of onset and determination of the selected complex and/or segment of the ECG signal. Accordingly, it is preferred to determine a standard length of the QRS complex for each lead of the standard 12-lead ECG, which is computed as a mean value of the lengths of all of the selected QRS complexes for the lead. In a particularly preferred embodiment, these up to twelve standard length values may be recorded and fixed for each individual patient whose ECG signals are analysed according to the method of the invention.

In a further alternative embodiment of the method, a selected fixed standard length may be used for the QRS complexes, the selected complex of said standard length being centred on the R peak. Suitable values of the fixed standard length are preferably 60, 80, 100 and/or 120 milliseconds.

HGI values corresponding to the ST segment may be computed using the same method. The time of onset of the ST segment is preferably determined as the minimum of the S trough according to the same method used to determine the time of termination of the QRS complex. That is, the time $T_s$ of onset of the ST segment is determined as:

$$A(t_{s-3}), A(t_{s-2}), A(t_{s-1}) > A(t_s) < A(t_{s+1}), A(t_{s+2}), A(t_{s+3})$$

wherein $A(t_i)$ is an amplitude of the ECG signal at the time corresponding to the $i^{th}$ sample point.

The termination time of the ST segment is determined by fixing the duration of the segment to one of the two so called "golden standard" values commonly employed by expert medical practitioners such as cardiologists. That is, the duration of the ST segment may be established as either 60 milliseconds or 80 milliseconds, depending upon the standard chosen.

Further processing of the extracted ST segment signals is conducted in the same manner as previously described for computing the HGI values based on the QRS complex.

Figure 4:
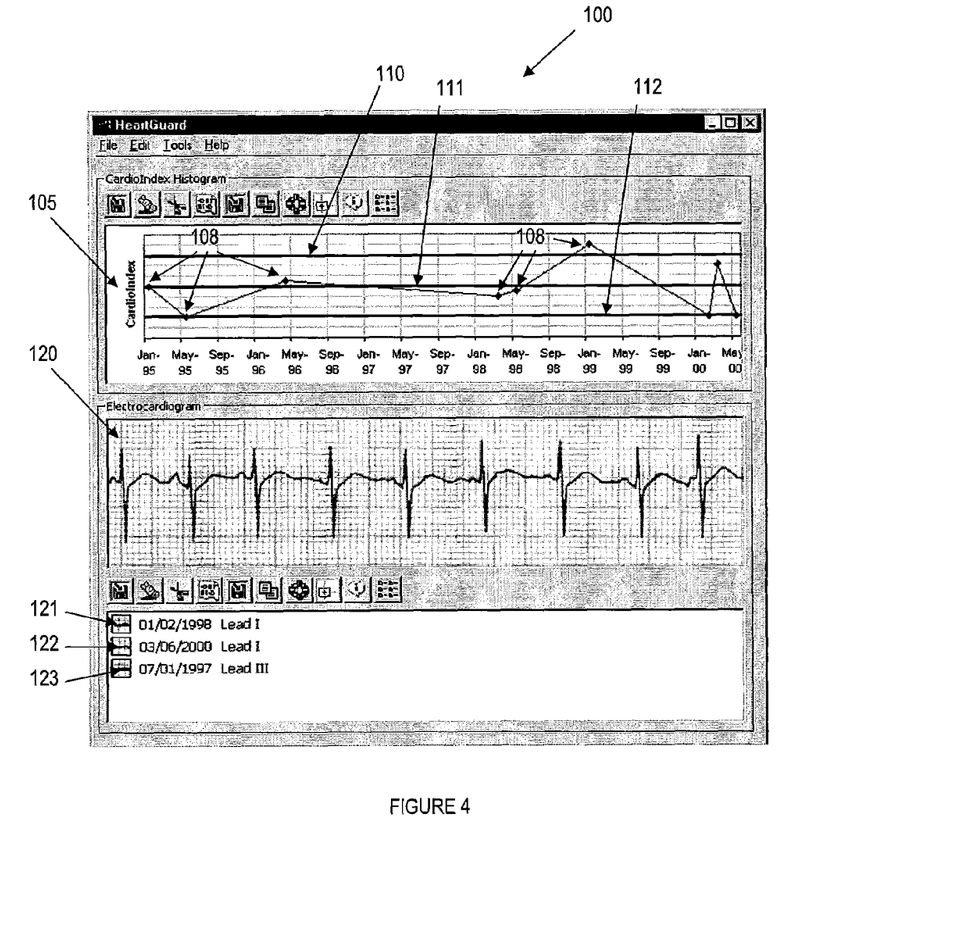
FIG. 4 is an example display screen of a software application running on the system for 30 processing electrocardial signals.

In accordance with preferred embodiments of the invention, the method 600 further includes performing a comparison 612 of the computed HGI values with historical data of the patient, and displaying 614 the comparative data in the form of a graph, as described in greater detail below with reference to FIG. 4.

Once an HGI value is generated by the computer system 10, it is displayed on display module 14. Shown in FIG. 4 is an interface 100 which is hosted by display module 14. The displayed HGI value may be the global $HGI_G$ value computed from analysis of the QRS complex, ST segment, or any other selected complex or segment. It may alternatively be any other HGI value, such as a regional HGI, $HGI_R$, computed from a single lead or combination of leads. Preferably, the operator is able to select from any such computed HGI values for display, as each may reveal different possible heart function abnormalities.

The interface 100 has an index display portion 105 for displaying different HGI values 108 generated over time. The index display portion 105 also includes a mean index line 111 which represents a normal or "average" index value for the particular patient under consideration. An upper bound line 110 and lower bound line 112 represent acceptable of upper and lower bounds for variation of the index values 108. Upper and lower bound lines 110, 112 represent a fixed deviation from mean index line 111, for example, such as a 10% deviation. The mean index line 111 is calculated as the mean of the HGI values over the full period (eg. 20 years) for which the HGI values are calculated from the stored (or real-time) ECG data.

Each of the index values 108 shown in the index display portion 105 represents an HGI value determined from ECG data taken at a particular time in the relevant patient's life. Some variation in magnitude of the index values 108 is natural over time, and in fact the mean index line 111 may change slightly to account for aging as the patient ages over long periods of time. In viewing the index display portion 105, the medical practitioner will take particular note of index values 108 which fall outside of the upper and lower bound lines 110, 112 as these exceptional values indicate that the heart may not be functioning in a healthy manner. Particularly where large deviation from the mean index line 111 is apparent, the medical practitioner will be alerted to the possibility of abnormal heart function and can take steps to further investigate any such possible abnormal functions.

An additional feature of the interface 100 is that it allows for display of an electrocardiogram 120 in response to selection by the medical practitioner of an index value 108 for a particular time. The electrocardiogram 120 corresponds to one of the stored ECG signals 121, 122, 123, which may correspond to different standard ECG leads and/or to ECG recordings of a patient taken at different times. For example, in FIG. 4, ECG signals 121, 122 correspond to signals derived from lead I recorded on two different dates, while ECG signal 123 corresponds to the signal derived from lead III on a third distinct date. The electrocardiogram 120 shown in FIG. 4 corresponds to only one of the three ECG signals from which the HGI value 108 is determined. Alternatively, the electrocardiogram 120 may correspond to signals from a lead not used in determining the HGI value.

The methods of the described embodiments may be executed locally or remotely, in software or hardware or a combination of both. It is not necessary that the analysis of the ECG signals 20 derived from a patient 8 be performed in real time. The gathered ECG signals may be stored and analysed at the convenience of the medical practitioner or even forwarded to other practitioners for their comment or analysis.

Figure 3:
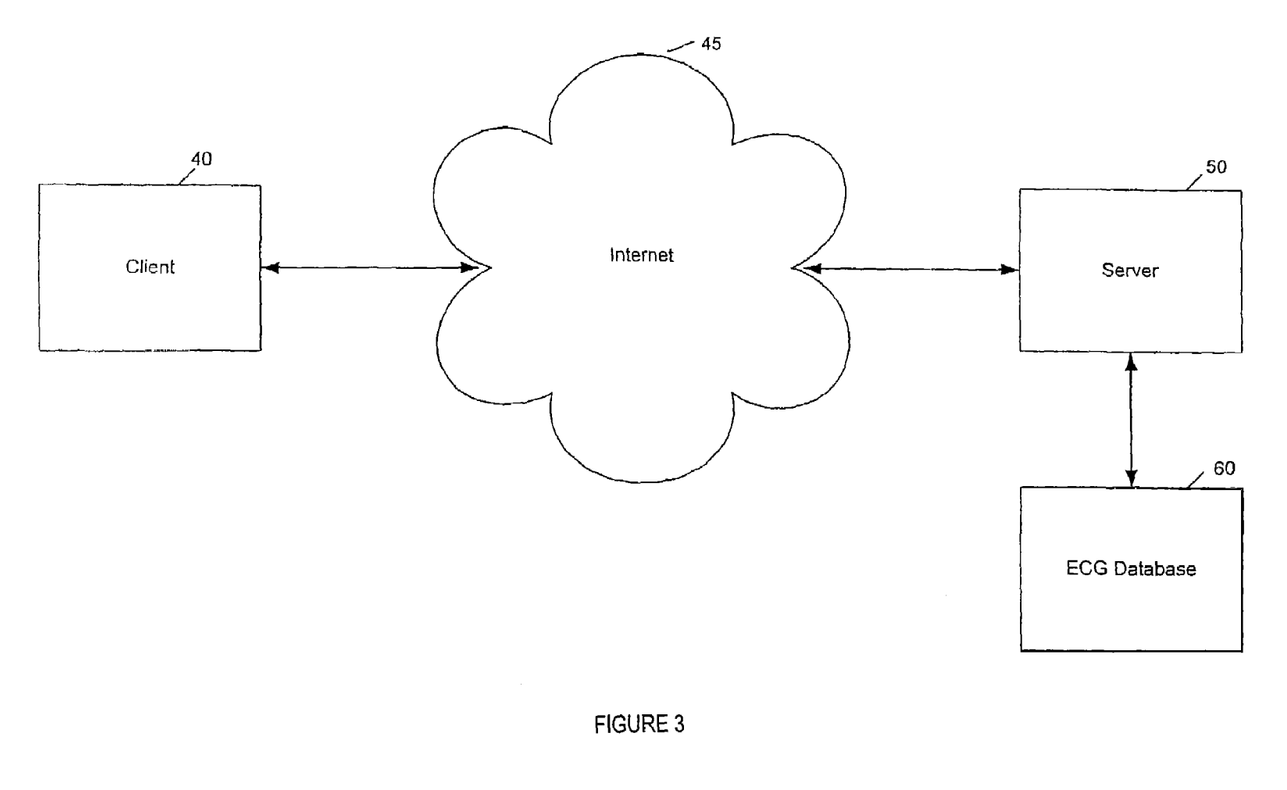
FIG. 3 is a block diagram of a client-server arrangement for use with a system for processing electrocardial signals.

Referring now to FIG. 3, embodiments of the invention are particularly suited to arrangements involving communication of the ECG data over a network for remote analysis. For example, a client 40, such as a medical practitioner may send gathered ECG data over a network 45, such as by uploading a file over the Internet, to a server 5 for storage or processing according to the invention. The server 50 in this sense performs a function analogous to the system 10 shown in FIG. 2 as it is adapted to perform signal processing functions on the received ECG data and to provide the output of such processing to a display module (not shown), either local to the server 50 or located at the client site 40. The server 50 communicates with an ECG database 60 for storing ECG data and HGI values generated from that data relating to a particular patient in a patient record. This enables medical practitioners to retrieve HGI data and ECG data, and view that data via interface 100 using a web browser, for example, thereby saving the medical practitioner the trouble of storing that patient information locally over a long period of time.

Additionally, the server 50 may provide HGI values or a display thereof (if the software is not installed locally to the client) back to the client 40 immediately in response to receiving ECG data therefrom. This enables the medical practitioner to view the HGI value generated from data which has just been recorded, together with HGI values and ECG traces from previous recordings (stored on the ECG database 60 but which are returned to the client 40 from the server 50 along with the newly generated HGI value).

The network 45 may take any appropriate form such as a local area network, wide area 30 network or other open or closed networks.

As communication and computer technology continues to improve, it is envisioned that the interface 100 can be provided on small wireless devices or other computer technology used by medical practitioners to view and analyse information generated according to embodiments of the invention.

Animal Studies

The QRS complex morphology normally plays relatively little part in cardiac diagnosis beyond ventricular hypertrophy and infarction, and conduction abnormalities. However, the QRS complex represents ventricular systole and thus is the correlate of the critical energy-utilising step within the cardiac cycle. It was therefore postulated by the inventors that detailed analysis of the energy generated within the QRS complex in the surface ECG may yield incremental physiological and/or pathophysiological information. Studies were therefore conducted to verify the usefulness of the Heart-Guard index as an indicator of cardiac health and an ECG marker.

Preclinical studies were undertaken in greyhounds and an experimental model was created to evaluate the sensitivity of the presently developed ECG data analysis technique (which outputs the HGI values).

Atrial and ventricular epicardial electrograms were recorded before and during LAD (left arterial descending vessel) occlusion; after 10 minutes of ischemia the ligature was released and recordings made following reperfusion. In order to obtain preliminary data regarding possible pathophysiological significance of the HGI as an ECG marker, electrocardiograms were analysed prior to, during, and after induction of regional ischemia. The findings reveal essentially the differences in the frequency spectral patterns of ventricular electrocardiograms between each of the recordings, namely control, ischemia, and reperfusion. The findings were independent of the time frame after onset of the electrocardiogram (40-120) ms. For each period of recorded electrocardiogram, HGI values were computed and in all animals ischemia produced a reversible decrease of HGI values with return to the control level after about five minutes of reperfusion. The results were the same irrespective of whether early parts of the ventricular electrogram of 40 ms in duration or up to 120 ms in duration were analysed. In summary, the HGI values tended to decrease during induction of ischemia, and returned towards normal during or following reperfusion.

Clinical Studies

Continuous 12-lead ECG monitoring is a commonly used tool for detecting episodes of myocardial ischaemia. Traditionally, changes to the ST-segment and the T-wave, as assessed by expert medical practitioners, have been utilised for detection of myocardial ischaemia/infarction.

It has been proposed by the inventors that the HGI may be a more sensitive indicator of acute coronary occlusion compared to ST-segment deviation.

Clinical studies were therefore conducted, the purpose of which was to determine the HGI values and to compare the incidence and magnitude of ST-segment and HGI changes during pacing-induced stress and percutaneous coronary angioplasty (PTCA) procedures.

High frequency QRS complex and ST-segment recordings were utilised to compare the sensitivity of the two different methods for detecting ischaemic episodes.

The clinical studies verified the usefulness of the HGI as an indicator of cardiac health and an ECG marker. Four investigations undertaken to date utilising ECG recordings have established the following results concerning the derived HGI value:

In young normal subjects, HGI values fluctuated minimally during normal routine activity or moderate exertion. The coefficient of variability on repeat estimates on different days was less than 10%.

In patients aged 40+ years with known coronary artery disease, HGI fluctuations over a 30-minute period preceding potential coronary angioplasty were over 20% in the absence of anginal symptoms.

Occlusions of a major epicardial coronary artery at angioplasty for 90-120 seconds lead to more than 25% fluctuation in HGI values, irrespective of presence/absence of S-T fluctuations.

The extent of the fluctuation in HGI values with atrial pacing-induced myocardial ischaemia tends to be significantly greater than in patients without tachycardia-induced ischaemia. HGI changes of more than 25% occurred only in patients with reversible ischaemia, the mean variation being 30%, as compared with only 8% in patients without the condition.

In summary, the studies demonstrated that changes in HGI values occur frequently in patients with known myocardial ischemia.

Fluctuations in HGI:

occur in some patients during coronary occlusion in the absence of diagnostic S-T segment changes; and appear to correlate with presence of inducible ischemia.

It was further concluded from the studies that continuous 12-lead ECG monitoring with computerised combined analysis of fluctuations in QRS-based global HGI ($HGI_G$) and regional HGI ($HGI_R$), and ST-based HGI ($HGI_{ST}$)

could provide a sensitive and specific means for early detection with the localization of myocardial ischaemia.

CONCLUSION

The use of the present methodology in heart assessment is advantageous due to its character as a practical non-invasive method of heart monitoring which provides an ECG marker as an indicator as to the presence of intracardiac events. The results of the studies suggest that ongoing HGI monitoring for an objective analysis of ECG will provide a medical practitioner with an early indication of possible problems.

The HGI permanent recording is advantageous for monitoring the health of a person's heart over his/her lifetime, with the required adjustments for the individuals' baseline (average/normal HGI values) being made periodically as effects such as aging, and therefore heart deteriorations progress. Fluctuations of the computed HGI values within or outside of an acceptable, time adjustable range provide a criterion for more detailed consideration of the individuals' heart condition by a medical practitioner.

Advantageously, embodiments of the invention allow for regular screening of a patient's cardiac health to be conducted so as to identify possible problems and allow for preventative therapy to be initiated. Additionally, if a patient undergoes therapy or treatment for a cardiac disorder, embodiments of the invention allow for monitoring of the patient during and/or after that treatment or therapy in order to quantify the impact or effectiveness of the treatment. Embodiments of the invention thus provide a medical practitioner with a view of the dynamic of the HGI values over time, allowing the practitioner to observe changes in a patient's cardiac health.

An additional advantage is provided by the availability of centralised storage and processing of ECG data as well as retrieval of historical ECG data, HGI values and related information over a network, regardless of the location of the patient.

The presently described method, system and apparatus constitute a useful tool for cardiac health assessment, allowing comparative analysis of the condition of the underlying cardiac anatomy and electrical functions for supporting clinical decision making.

What is claimed is:

1. A method of processing electrocardiogram (ECG) signals in order to identify a possible abnormality of heart function of a patient, the method comprising the steps of:
    extracting data from at least one ECG signal;
    determining a time derivative of said data;
    generating a normalised index value representative of energy in said time derivative;
    comparing said normalised index value with a mean value calculated as a numerical average of a plurality of prior normalised index values generated from ECG signal data of the patient gathered over a plurality of prior time periods,
    wherein said step of comparing comprises ascertaining whether the normalised index value lies within a range between an upper bound value greater than said mean value, and a lower bound value less than said mean value less than said mean value and,
        if the normalised index value is below said range, identifying a possible abnormality of heart function of the patient;
        if the normalised index value is above said range, identifying a possible abnormality of heart function of the patient; and
    outputting a result of said comparing comprising said identification of a possible abnormality of heart function of the patient where the normalised index value is below or above said range to one or more of a memory device, a display, or a remote apparatus accessible via a communications network.

2. The method of claim 1 wherein the step of generating a normalised index value comprises:
    determining frequency components of said time derivative; and
    calculating a normalised index value representative of the energy in said frequency components.

3. The method of claim 2 wherein the step of determining frequency components includes computing a Fourier transform of said time derivatives.

4. The method of claim 3 wherein said Fourier transform is computed using a Fast Fourier Transform (FFT) algorithm.

5. The method of claim 3 wherein said Fourier transform is a discrete Fourier transform.

6. The method of claim 5 wherein said discrete Fourier transform is a 512 point discrete Fourier transform.

7. The method of claim 2 wherein the step of calculating a normalised index value comprises calculating a normalised sum of the squares of the magnitudes of said frequency components.

8. The method of claim 1 wherein said ECG signals comprise signals from any one or more of up to 12 leads of a standard 12-lead ECG.

9. The method of claim 1 wherein said normalised index value is computed according to:

$$\text{normalised index value} = \sum_R \left\{ \frac{1}{n} \sum_{i=1}^{n} F_i^2 \right\}$$

wherein:
    R represents one or more of up to 12 leads of a standard 12-lead ECG;
    $F_i$ represents the magnitude of frequency components of said time derivative; and
    n is the total number of said frequency components.

10. The method of claim 1 wherein the step of extracting comprises the steps of:
    determining the times of onset and termination of selected complexes and/or segments of said ECG signals; and
    copying each of said selected complexes and/or segments into a data record to create said extracted data.

11. The method of claim 10 wherein said selected complexes and/or segments comprise QRS complexes of said ECG signals.

12. The method of claim 11 wherein the step of determining the times of onset and termination of a selected QRS complex comprises identifying local minima in the ECG signal corresponding to the points Q and S according to the equations:

$$A(t_{q-3}), A(t_{q-2}), A(t_{q-1}) > A(t_q) < A(t_{q+1}), A(t_{q+2}), A(t_{q+3})$$

$$A(t_{s-3}), A(t_{s-2}), A(t_{s-1}) > A(t_s) < A(t_{s+1}), A(t_{s+2}), A(t_{s+3})$$

wherein $A(t_i)$ is an amplitude of the ECG signal at the time corresponding to the $i^{th}$ sample point, $t_q$ is the time of onset of the QRS complex corresponding to the point Q, and $t_s$ is the time of termination of the QRS complex corresponding to the point S.

13. The method of claim 12 wherein said ECG signals comprise signals from any one or more of up to 12 leads of a standard 12-lead ECG, and a standard duration of a selected QRS complex is determined for each of said leads as the average of the time intervals between the time of onset and the time of termination of a plurality of ECG signals received from each of said leads.

14. The method of claim 11 wherein said ECG signals comprise signals from any one or more of up to 12 leads of a standard 12-lead ECG recorder, and a standard duration of a selected QRS complex is one of 60 milliseconds, 80 milliseconds, 100 milliseconds or 120 milliseconds, and the times of onset and termination of said selected QRS complex are determined such that the selected complex is centred on an R peak of the ECG signal.

15. The method of claim 10 wherein the selected complexes and/or segments comprise ST segments of ECG signals.

16. The method of claim 15 wherein the time of onset of said ST segments is determined as the time $t_s$ of a local minimum in the ECG signal corresponding to point S according to the equation:

$$A(t_{s-3}), A(t_{s-2}), A(t_{s-1}) > A(t_s) < A(t_{s+1}), A(t_{s+2}), A(t_{s+3})$$

wherein $A(t_i)$ is an amplitude of the ECG signal at the time corresponding to the $i^{th}$ sample point.

17. The method of claim 15 wherein the duration of each of said ST segments is 60 milliseconds.

18. The method of claim 15 wherein the duration of each of said ST segments is 80 milliseconds.

19. The method of claim 1 wherein said step of extracting includes sampling said ECG signal to provide digitized ECG signals.

20. The method of claim 19 wherein said sampling is carried out at a sample rate of approximately 1000 Hz.

21. An apparatus for processing electrocardiogram (ECG) signals in order to identify a possible abnormality of heart function of a patient, the apparatus comprising:
- an extractor for extracting data from at least one ECG signal;
- a differentiator for determining a time derivative of said data;
- an index value generator for generating a normalised index value representative of energy in said time derivative;
- means for comparing said normalised index value with a mean value calculated as a numerical average of a plurality of prior normalised index values generated from ECG signal data of the patient gathered over a plurality of prior time periods, to ascertain whether the normalised index value lies within a range between an upper bound value greater than said mean value and a lower bound value less than said mean value and,
  - if the normalised index value is below said range, identifying a possible abnormality of heart function of the patient; and
  - if the normalised index value is above said range, identifying a possible abnormality of heart function of the patient; and
- means for outputting a result of said comparing to one or more of a memory device, a display, or a remote apparatus accessible via a communications network.

22. The apparatus of claim 21 wherein the index value generator comprises:
- a spectrum calculator for determining frequency components of said time derivative; and
- an index value calculator for calculating a normalised index value representative of the energy in said frequency components.

23. The apparatus of claim 22 wherein the spectrum calculator determines frequency components of said time derivative by computing a Fourier transform of said time derivative using a Fast Fourier Transform (FFT) algorithm.

24. The apparatus of claim 22 wherein the index value calculator calculates a normalised sum of the squares of the magnitudes of the frequency components determined by the spectrum calculator.

25. The apparatus of claim 21 wherein the ECG signals comprise signals from any one or more of up to 12 leads of a standard 12-lead ECG recorder, and the index value generator computes a normalised index value according to the equation:

$$\text{normalised index value} = \sum_R \left\{ \frac{1}{n} \sum_{i=1}^{n} F_i^2 \right\}$$

wherein:
- R represents one or more of up to 12 leads of a standard 12-lead ECG;
- $F_i$ represents the magnitude of frequency components of said time derivative; and
- n is the total number of said frequency components.

26. The apparatus of claim 21 wherein the extractor determines the times of onset and termination of selected complexes and/or segments in said ECG signals, and copies each of said selected complexes and/or segments sequentially into a data record to create said extracted data.

27. The apparatus of claim 26 wherein said selected complexes and/or segments comprise QRS complexes of said ECG signals.

28. The apparatus of claim 26 wherein said selected complexes and/or segments comprise ST segments of said ECG signals.

29. A method of identifying possible abnormalities of heart function of a patient comprising:
- extracting data from each of a plurality of electrocardiogram (ECG) signals of said patient gathered over a plurality of respective time periods;
- determining a plurality of respective time derivatives of said extracted data;
- generating a plurality of respective normalised index values representative of the energy in said time derivatives;
- comparing said normalised index values over said plurality of time periods to identify possible abnormalities of heart function of said patient,
- wherein said step of comparing includes calculating a mean value as a numerical average of said normalised index values, calculating an upper bound value which is greater than said mean value, and calculating a lower bound value which is less than said mean value, ascertaining whether each of said normalised index values lies within a range between said upper and lower bound values; and
  - a) if the normalised index value is below said range, identifying possible abnormalities of heart function of said patient;
  - b) if the normalised index value is above said range, identifying possible abnormalities of heart function of said patient; and
- outputting a result of said comparing to one or more of a memory device, a display, or a remote apparatus accessible via a communications network.

30. The method of claim 29 wherein said step of outputting includes generating a graph of said normalised index values as a function of time.

31. The method of claim 30 wherein said graph includes indications of said mean value, said upper bound value and said lower bound value.

32. The method of claim 29 wherein said upper and lower bound values are calculated as values representing a specified fractional deviation from said mean value.

33. The method of claim 32 wherein said fractional deviation is a 10% deviation.

34. The method of claim 29 wherein said step of comparing includes identifying possible abnormalities of heart function of said patient if one or more said normalised index values falls outside the range bounded by said upper and lower bound values.

35. A system for identifying possible abnormalities of heart function of a patient comprising:
- an extractor for extracting data from each of a plurality of electrocardiogram (ECG) signals of said patient gathered over a plurality of respective time periods;
- a differentiator for determining a plurality of respective time derivatives of said extracted data;
- an index value generator for generating a plurality of respective normalised index values representative of the energy in said time derivatives;
- comparing means for comparing said normalised index values over said plurality of time periods to identify possible abnormalities of heart function of said patient, wherein said comparing means is configured to calculate a mean value as a numerical average of said normalised index values, to calculate an upper bound value which is greater than said mean value, and to calculate a lower bound value which is less than said mean value, to ascertain whether each of said normalised index values lies within a range between said upper and lower bound values and, if the normalised index value is below the range, to identify possible abnormalities of heart function of said patient and, if the normalised index is above the range, to identify possible abnormalities of heart function of said patient; and means for outputting a result of said comparing to one or more of a memory device, a display, or a remote apparatus accessible via a communications network.

36. The system of claim 35 which wherein said outputting means comprises a computer having a display which is configured to generate a graph of said normalised index values as a function of time on said display.

37. The system of claim 36 which is further configured to include indications of said mean value, said upper bound value and said lower bound value, on the graph displayed on said display.

38. A system for processing electrocardiogram (ECG) signals of a patient comprising:
  a server computer system configured to receive digitized ECG signals over a data network, and including a processor configured to perform the steps of:
    extracting data from at least one ECU signal;
    determining a time derivative of said extracted data;
    generating a normalised index value representative of the energy in said time derivative; and
    comparing said normalised index value with a mean value calculated as a numerical average a plurality of prior normalised index values generated from ECG signal data of the patient gathered over a plurality of prior time periods,
  wherein said step of comparing comprises ascertaining whether the normalised index value lies within a range between an upper bound value greater than said mean value and a lower bound value less than said mean value, and, if the normalised index value is below said range, identifying a possible abnormality of heart function of the patient and, if the normalised index value is above the range, to identify possible abnormalities of heart function of said patient;

and wherein the system further comprises a database associated with said server for storing said normalised index values and/or digitized ECU signals in a data record of said patient.

39. A system for gathering electrocardiogram (ECU) signals of a patient for processing, said system comprising:
  ECG apparatus for monitoring and digitizing ECU signals of said patient; and
  a client computer system configured to receive digitized ECG signals from said ECG apparatus, and to transmit said digitized ECG signals over a data network to a server computer system,
  said server including a processor configured to perform the steps of:
    extracting data from said digitized ECG signal;
    determining a time derivative of said extracted data;
    generating a normalised index value representative of the energy in said time derivative;
    comparing said normalised index value with a mean value calculated as a numerical average of a plurality of prior normalised index values generated from ECG signal data of the patient gathered over a plurality of prior time periods,
  wherein said step of comparing comprises ascertaining whether the normalised index value lies within a range between an upper bound value greater than said mean value, and a lower bound value less than said mean value wherein if the normalised index value is below said range a possible abnormality of heart function of the patient is identified, and wherein if the normalised index value is above said range a possible abnormality of heart function is identified; and
  outputting a result of said comparing to one or more of a memory device, a display, or a remote apparatus accessible via a communications network.

40. The system of claim 39 wherein said client is further configured to receive one or more generated normalised index values from said server, and to display a graph of said normalised index values to enable a user of said client to identify possible abnormalities of heart function of said patient.

41. The system of claim 40 wherein said graph includes indications of said mean value, said upper bound value and said lower bound value.

* * * * *

UNITED STATES PATENT AND TRADEMARK OFFICE
CERTIFICATE OF CORRECTION

PATENT NO. : 7,412,283 B2 Page 1 of 1
APPLICATION NO. : 10/865985
DATED : August 12, 2008
INVENTOR(S) : Ginzburg et al.

It is certified that error appears in the above-identified patent and that said Letters Patent is hereby corrected as shown below:

1. Column 19, line 29, delete "ECU" and substitute --ECG-- therefor.

2. Column 20, line 3, delete "ECU" and substitute --ECG-- therefor.

3. Column 20, line 5, delete "ECU" and substitute --ECG-- therefor.

4. Column 20, line 7, delete "ECU" and substitute --ECG-- therefor.

Signed and Sealed this

Thirtieth Day of September, 2008

JON W. DUDAS
*Director of the United States Patent and Trademark Office*